United States Patent
Etchegaray et al.

(10) Patent No.: US 8,652,516 B1
(45) Date of Patent: Feb. 18, 2014

(54) DOXYCYCLINE FORMULATIONS, AND METHODS OF TREATING ROSACEA

(71) Applicants: Galderma S.A., Lausanne 30 Grey (CH); Cerovene, Inc., Valley Cottage, NY (US)

(72) Inventors: Jean-Pierre Etchegaray, Nice (FR); Nathalie Wagner, Pegomas (FR); Manish S. Shah, West Caldwell, NJ (US); Ray J. Difalco, Ridgewood, NJ (US)

(73) Assignees: Cerovene, Inc., Valley Cottage, NY (US); Galderma S.A., Lausanne 30 Grey (CH)

( * ) Notice: Subject to any disclaimer, the term of this patent is extended or adjusted under 35 U.S.C. 154(b) by 0 days.

(21) Appl. No.: 13/929,598

(22) Filed: Jun. 27, 2013

Related U.S. Application Data

(60) Provisional application No. 61/794,030, filed on Mar. 15, 2013.

(51) Int. Cl.
*A61K 9/24* (2006.01)
*A61K 9/52* (2006.01)

(52) U.S. Cl.
USPC ............ 424/463; 424/451; 424/457; 424/458

(58) Field of Classification Search
USPC .......................................... 424/451, 457–463
See application file for complete search history.

(56) References Cited

U.S. PATENT DOCUMENTS

2012/0244216 A1* 9/2012 Shah et al. .................... 424/452

OTHER PUBLICATIONS

FDA guidance (Bioavailability and Bioequivalence Studies for Orally Administered Drug Products—General Considerations—Mar. 2003).*

* cited by examiner

*Primary Examiner* — Michael G Hartley
*Assistant Examiner* — Micah-Paul Young
(74) *Attorney, Agent, or Firm* — Hoffmann & Baron, LLP

(57) ABSTRACT

The present invention is directed to a pharmaceutical composition in unit dose form for orally delivering doxycycline to a human, the pharmaceutical composition comprising: a capsule, wherein the capsule is coated with a delayed release layer; wherein the delayed release layer comprises about 4 to 6 mg of doxycycline monohydrate and a binding agent, and wherein the delayed release layer is coated with an enteric coating; wherein the enteric coating dissolves at pH of about 5 to 6, and wherein the enteric coating is coated with an immediate release layer; wherein the immediate release layer comprises about 32 mg of doxycycline monohydrate and a binding agent, wherein the relative mean $C_{max}$ of the pharmaceutical composition is within 80.00% to 125.00% of a $C_{max}$ value of 510±220.7 ng/mL, after administration of a single dose of the pharmaceutical composition to humans in a fasting state; and wherein the relative mean $AUC_{(0-\infty)}$ of the pharmaceutical composition is within 80.00% to 125.00% of a $AUC_{(0-\infty)}$ value of 9227±3212.8 ng·hr/mL, after administration of a single dose of the pharmaceutical composition to humans in a fasting state.

29 Claims, 8 Drawing Sheets

Mean (± SD) Plasma Doxycycline Concentration vs. Time Profiles using Normal scale Mean (± SD) Plasma Doxycycline Concentration vs. Time Profiles in Log-linear Scale Figure 6  Dissolution profiles – Doxycycline coated capsules, 40 mg vs. Oracea capsules, 40 mg
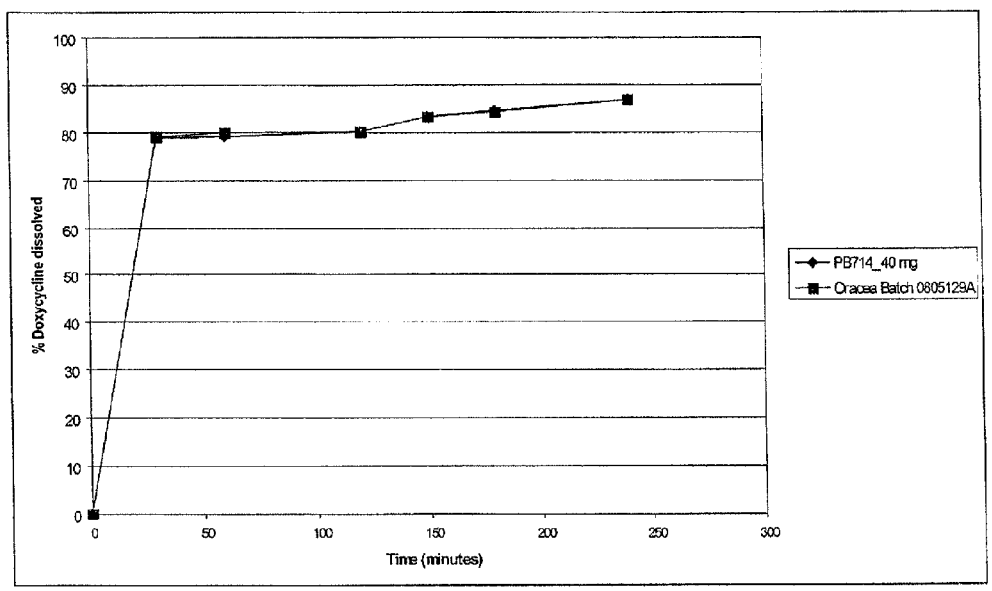

Figure 7 — Dissolution profiles – Capsules coated with 4 mg and 6 mg doxycycline – Delayed release layer
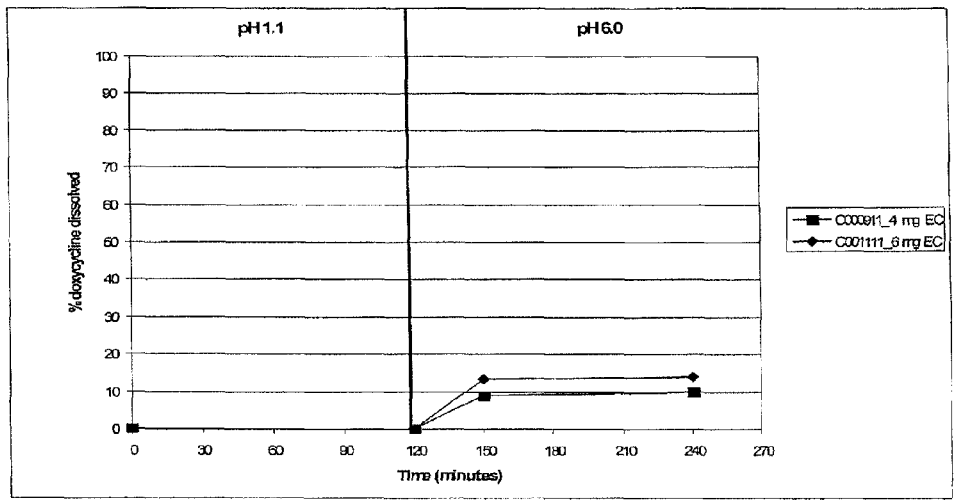
Note: % of doxycycline dissolved are expressed as % of the final label claim (36 or 38 mg)
Figure 8 - Dissolution profiles - Capsules coated with 36 mg and 38 mg doxycycline – Finished Drug Product
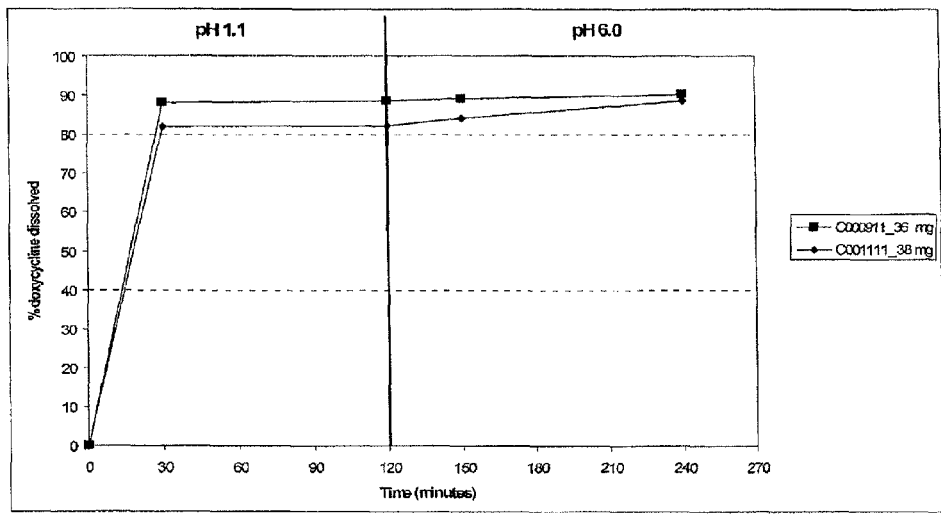

Figure 9  Pharmacokinetic study (BE09/040 and BE09/041) – Doxycycline coated capsules 40 mg versus Oracea® capsules 40 mg
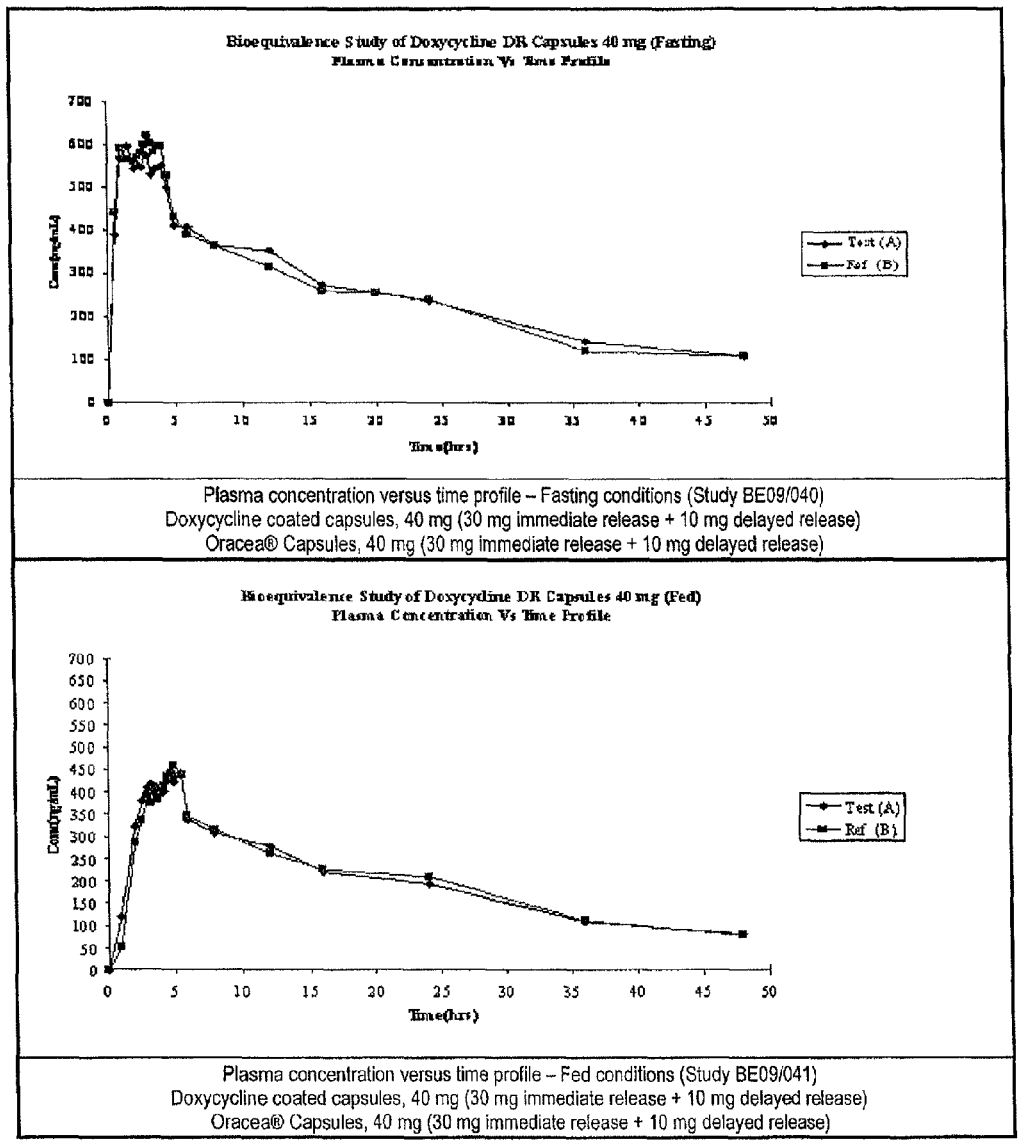

Figure 10   Pharmacokinetic study (BE09/060 and BE09/061) – Doxycycline coated capsules 36 mg versus Oracea® capsules 40 mg
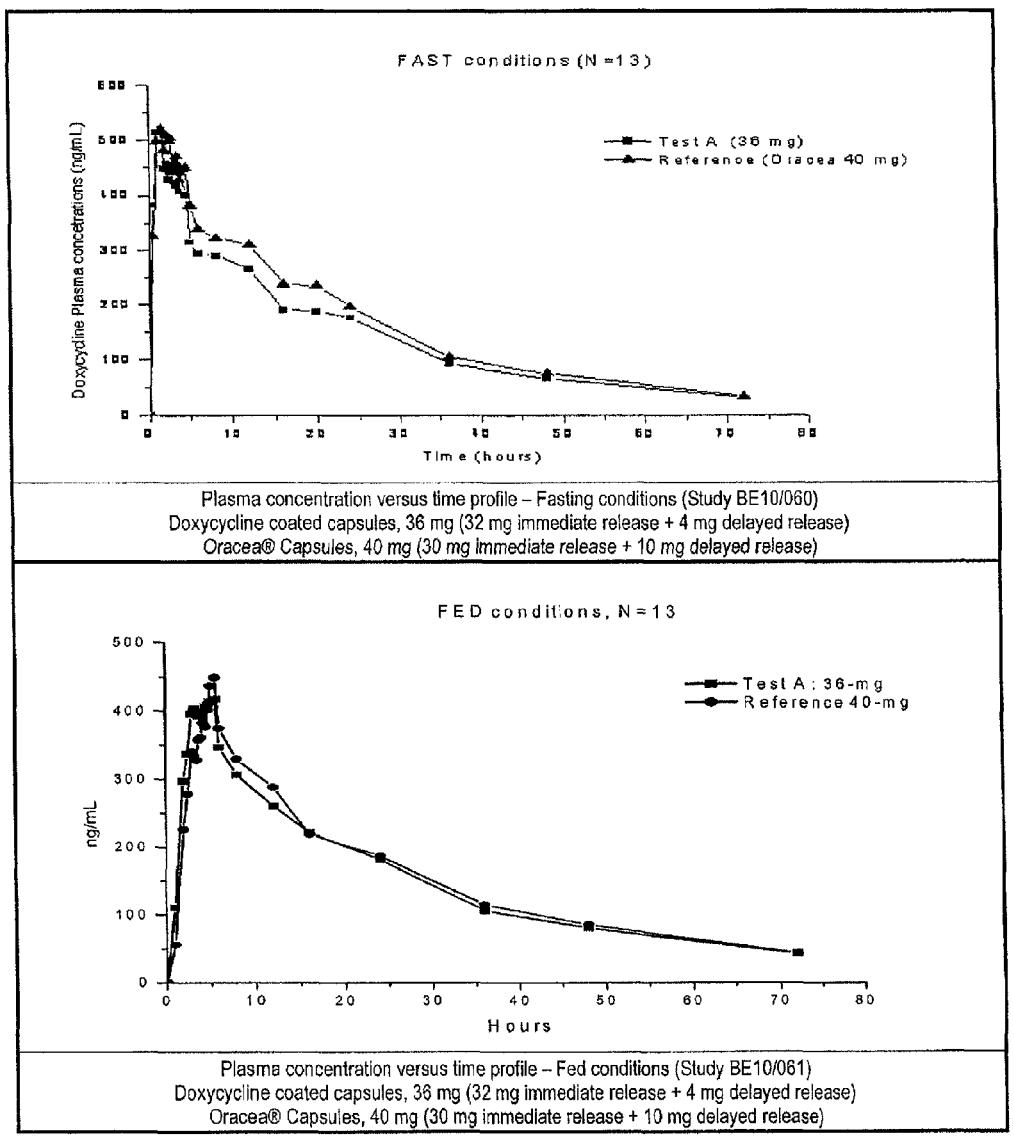

Figure 11   Pharmacokinetic study (BE09/060 and BE09/061) – Doxycycline coated capsules 37.5 mg versus Oracea® capsules 40 mg
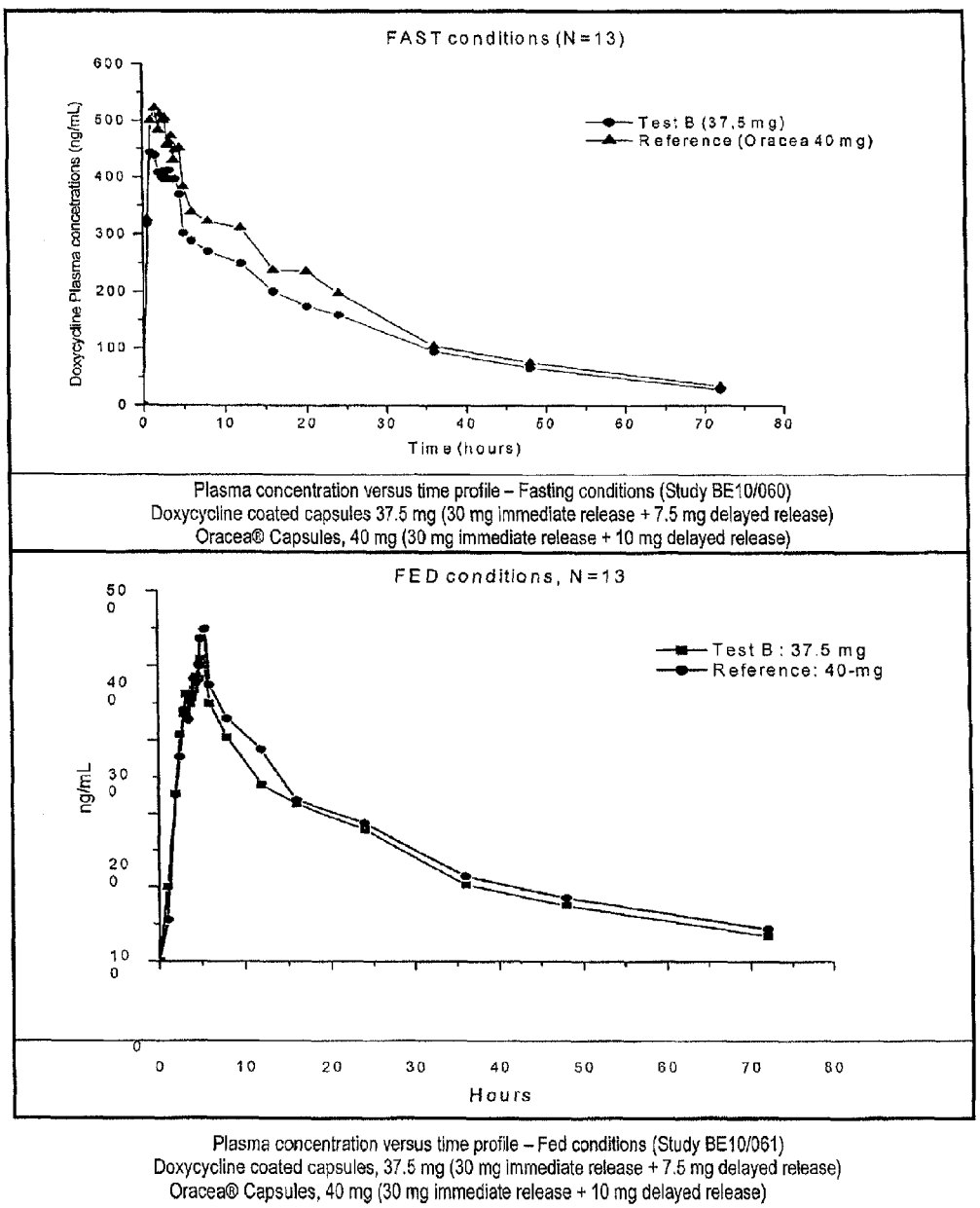

DOXYCYCLINE FORMULATIONS, AND METHODS OF TREATING ROSACEA

CROSS-REFERENCE TO RELATED APPLICATION

This application claims the benefit of U.S. Provisional Application No. 61/794,030, filed Mar. 15, 2013, which is incorporated herein by reference in its entirety.

BACKGROUND OF THE INVENTION

Rosacea is a chronic condition characterized by facial erythema and skin lesions. Rosacea typically begins as redness on the central face across the cheeks, nose, or forehead, but can also less commonly affect the neck, chest, ears, and scalp. Symptoms, such as semi-permanent redness, telangiectasia, red domed papules and pustules, and in some advanced cases, a red lobulated nose (rhinophyma), may develop.

Although there are effective treatments for rosacea on the market (e.g., Oracea® sold by Galderma Laboratories, L.P.), formulations with reduced active ingredients are desirable.

BRIEF DESCRIPTION OF THE DRAWINGS

FIG. 6 is a graph showing Dissolution profiles of Doxycycline coated capsules, 40 mg versus Oracea® capsules, 40 mg.

FIG. 7 is a graph showing Dissolution profiles of Capsules coated with 4 mg and 6 mg doxycycline: Delayed release layer.

FIG. 8 is a graph showing Dissolution profiles of Capsules coated with 36 mg and 38 mg doxycycline: Finished Drug Product.

FIG. 9 is a graph showing a Pharmacokinetic study of Doxycycline coated capsules 40 mg versus Oracea® capsules, 40 mg.

FIG. 10 is a graph showing a Pharmacokinetic study of Doxycycline coated capsules 36 mg versus Oracea® capsules, 40 mg.

FIG. 11 is a graph showing a Pharmacokinetic study of Doxycycline coated capsules 37.5 mg versus Oracea® capsules, 40 mg.

SUMMARY OF THE INVENTION

Figure 1:
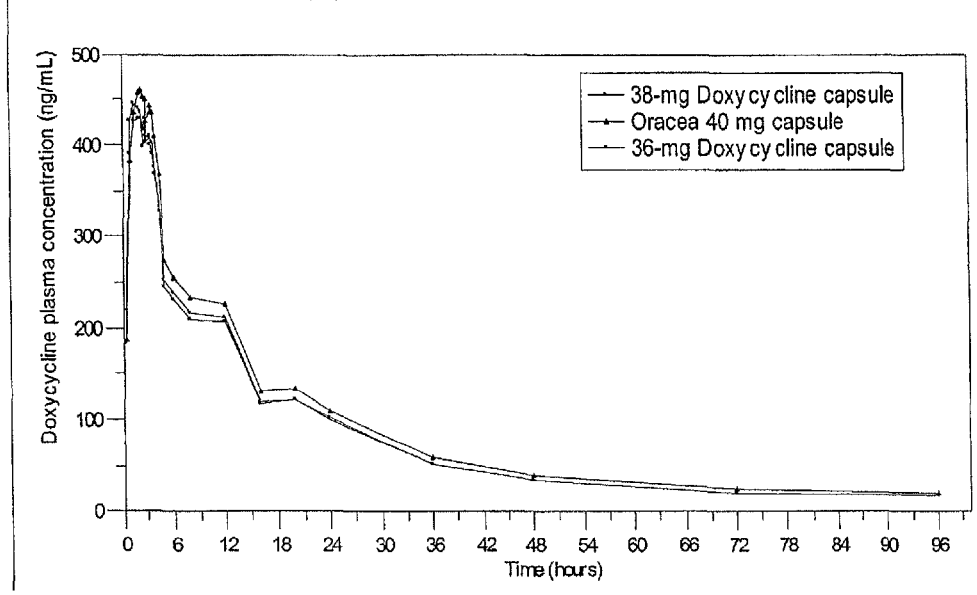
FIG. 1 is a graph showing the Mean (±SD) Plasma Doxycycline Concentration vs. Time Profiles using Normal scale.

In one embodiment, the present invention provides a pharmaceutical composition in unit dose form for orally delivering doxycycline to a human. The pharmaceutical composition comprises a coated capsule. The capsule is coated with a delayed release layer, enteric coating and an immediate release layer. The delayed release layer comprises about 4 to 6 mg of doxycycline, or a pharmaceutically acceptable salt thereof, and a binding agent. The delayed release layer is coated with an enteric coating. The enteric coating dissolves at pH of about 5 to 6. The enteric coating is coated with an immediate release layer. The immediate release layer comprises about 32 mg of doxycycline, or a pharmaceutically acceptable salt thereof, and a binding agent.

In one embodiment, the mean $C_{max}$ of the pharmaceutical composition is within about 80.00% to 125.00% of a $C_{max}$ value of about 510±220.7 ng/mL (or about 80% to 125% of a $C_{max}$ value in the range of about 290 ng/mL to 730 ng/mL), after administration of a single dose of the pharmaceutical composition to humans in a fasting state. The mean $AUC_{(0-\infty)}$ of the pharmaceutical composition is within about 80.00% to 125.00% of a $AUC_{(0-\infty)}$ value of about 9227±3212.8 ng·hr/mL (or about 80% to 125% of a $AUC_{(0-\infty)}$ value in the range of about 6010 ng·hr/mL to 12,440 ng·hr/mL), after administration of a single dose of the pharmaceutical composition to humans in a fasting state.

The mean $C_{max}$ of the pharmaceutical composition at steady state is within about 80.00% to 125.00% of a $C_{max}$ value of about 600±194.2 ng/mL (or about 80% to 125% of a $C_{max}$ value in the range of about 405 ng/mL to 795 ng/mL), after administration to humans in a fasting state, and the relative mean $AUC_{(0-t)}$ of the pharmaceutical composition at steady state is within about 80.00% to 125.00% of a $AUC_{(0-t)}$ value of about 7543±2443.9 ng·hr/mL (or about 80% to 125% of a $AUC_{(0-t)}$ value in the range of about 5090 ng·hr/mL to 9990 ng·hr/mL), after administration to humans in a fasting state.

Preferably, the doxycycline monohydrate is micronized. In one embodiment, the micronized doxycycline monohydrate has less than about 10 μm distribution for at least about 90% of particles.

In one embodiment, the pharmaceutical composition further comprises a seal coating between the capsule and the delayed release coating. In one embodiment, the seal coating comprises a pH dependent ingredient, wherein the pH dependent ingredient dissolves at pH of about 5 to 6.

The capsule contains about 200 mg to about 260 mg of at least one inert ingredient. Preferably, the capsule does not contain an active ingredient. Preferably, the capsule is hydroxypropyl methylcellulose.

The ratio of the binding agent to the doxycycline monohydrate in the delayed release layer is about 1:3. The ratio of the binding agent to the doxycycline monohydrate in the immediate release layer is about 1:3. Preferably, the binding agent is hydroxypropyl methylcellulose (HPMC), hydroxyethyl cellulose (HEC), hydroxypropyl cellulose (HPC), carboxy methyl cellulose (CMC), or mixtures thereof. More preferably, the binding agent is hydroxypropyl methylcellulose (HPMC).

The pharmaceutical composition has a dissolution profile such that about 80% to about 90% of the doxycycline monohydrate is dissolved after about 30 minutes at pH of about 1.1. The pharmaceutical composition has a dissolution profile such that about 90% of the doxycycline monohydrate is dissolved after about 120 minutes at pH of about 1.1 and 120 minutes at pH of about 6.0.

In one embodiment, the pharmaceutical composition further comprises an outer color coating.

In another embodiment, the present invention provides a method for treating papules and pustules of rosacea in a human in need thereof, comprising orally administering a once a day dose of a pharmaceutical compositions of the present invention to the human.

DETAILED DESCRIPTION OF THE INVENTION

The present invention is directed to pharmaceutical compositions that produce a sustained release profile of doxycycline, and methods of using the pharmaceutical compositions to treat disorders, in particular rosacea.

Throughout this specification, quantities are defined by ranges, and by lower and upper boundaries of ranges. Each lower boundary can be combined with each upper boundary to define a range. The lower and upper boundaries should each be taken as a separate element.

The pharmaceutical compositions of the present invention are preferably provided in unit dose form and are formulated for oral delivery of doxycycline to humans. In one embodiment, the unit dose form of the pharmaceutical composition comprises a hard or soft capsule containing a fill. The fill consists of, or consists essentially of, one or more inert ingredients in a pharmaceutically acceptable vehicle. The capsule is coated by at least two separate layers comprising doxycycline.

The manufacture of hard or soft capsules is generally known by those of ordinary skill in the art. For example, soft capsules may be made by various processes including the plate process, the rotary die process, the reciprocating die process, and the continuous process. Examples of the capsular materials include, but are not limited to, natural or synthetic gelatin, pectin, casein, collagen, protein, modified starch, polyvinyl pyrrolidone, acrylic polymers, cellulose derivatives (such as, but not limited to, hydroxypropyl methylcellulose (HPMC)), and combinations thereof, optionally with one or more plasticizers and/or water. Capsular materials may also include one or more preservatives, coloring and opacifying agents, flavorings and sweeteners, sugars, gastroresistant substances, or combinations thereof.

The shape and size of the capsules can vary. The shape of the capsule may be, but is not limited to, round, oval, tubular, oblong, twist off, or a non-standard shape, preferably oblong. The size of the capsule used will vary in accordance to the volume of the fill composition intended to be contained therein. The various standard sizes of capsules are conventionally designated as (000), (00), (0), (1), (2), (3), (4), and (5).

The preferred material for a capsule of the present invention is one that retains doxycycline, or a pharmaceutically acceptable salt thereof, well and is not sensitive to temperature. An example of such is a HPMC capsule. Also, the preferred capsule has an oval shape and is of size designation (2).

The capsules are filled with pharmaceutically acceptable inert ingredients. These ingredients typically function to provide weight to the capsules so they do not fly around during coating processes. The term "inert ingredient" refers to any compound or compounds which do not have, or substantially do not have, pharmacological or biological activity. The capsules preferably do not contain any active ingredients. The capsules of the present invention are typically filled with about 100 to about 300 mg, more typically, about 150 to about 250 mg, and most typically about 200 mg of inert ingredients.

Examples of inert ingredients include excipients, diluents, disintegrants, surfactants, lubricants, and glidants. Preferred inert ingredients in the present invention include pregelatinized starch, lactose monohydrate and microcrystalline cellulose. A preferred lubricant is magnesium stearate.

The capsule of the present invention is coated with at least three layers. In particular, the capsule is coated with a delayed release layer, which is coated with an enteric coating, which is coated with an immediate release layer.

The delayed release layer and the immediate release layer contain doxycycline. Doxycycline can be in the form of a pharmaceutically acceptable salt. The term "pharmaceutically acceptable salt" refers to a salt prepared from doxycycline and pharmaceutically acceptable non-toxic acids or bases. The acids may be inorganic or organic acids of doxycycline. Examples of inorganic acids include hydrochloric, hydrobromic, hydroiodic, sulfuric, and phosphoric acids. Examples of organic acids include carboxylic and sulfonic acids. The radical of the organic acids may be aliphatic or aromatic. Some examples of organic acids include formic, acetic, phenylacetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, tartaric, citric, gluconic, gulonic, arylsulfonic, and galacturonic acids. Appropriate organic bases may be selected, for example, from N,N-dibenzylethylenediamine, chloroprocaine, choline, diethanolamine, ethylenediamine, meglumine (N-methylglucamine), and procaine.

Doxycycline is preferably administered as its hyclate salt or as a hydrate, preferably monohydrate.

The delayed release layer comprises doxycycline, or a salt thereof, and a binding agent. Examples of binding agents include cellulose polymers, such as, various grades of microcrystalline cellulose, hydroxypropyl methylcellulose (HPMC), hydroxyethyl cellulose (HEC), hydroxypropyl cellulose (HPC), carboxy methyl cellulose (CMC), sodium carboxymethylcellulose, and mixtures thereof. Hydroxypropyl methylcellulose (HPMC) is preferred as the binding agent in the present invention.

In one embodiment, the delayed release layer comprises about 4 mg of a doxycycline, or a pharmaceutically acceptable salt thereof (e.g., doxycycline monohydrate). In another embodiment, the delayed release layer comprises about 6 mg of a doxycycline, or a pharmaceutically acceptable salt thereof (e.g., doxycycline monohydrate). Typically, the ratio of a binding agent to a doxycycline salt is about 1:3.

The delayed release layer may further comprise anti-foaming agents, such as, for example, a simethicone emulsion. Typically, the ratio of a binding agent and anti-foaming agent to a doxycycline salt is about 1:3.

The delayed release layer is coated with an enteric coating. The enteric coating dissolves at pH of about 5 to 6, preferably at pH 5.5. An example of a preferred enteric coating is an aqueous dispersion of anionic polymers with methacrylic acid as a functional group. For instance, Eudragit® L30-55 can be used in the enteric coating. Additionally, the enteric coating may further comprise plasticizers. An example of a preferred plasticizer is triethylcitrate.

The enteric coating is coated with an immediate release layer. The immediate release layer comprises about 32 mg of a doxycycline, or a pharmaceutically acceptable salt thereof (e.g., doxycycline monohydrate), and a binding agent. Typically, the ratio of a binding agent to a doxycycline salt is about 1:3.

The immediate release layer may further comprise anti-foaming agents, such as, for example, a simethicone emulsion. Typically, the ratio of a binding agent and anti-foaming agent to a doxycycline salt is about 1:3.

In a preferred embodiment, the doxycycline salt of the present invention is micronized. For example, micronized doxycycline monohydrate can have less than about 10 μm distribution for at least about 70% of particles, for at least about 80% of particles, more typically for at least about 90% of particles, and most typically, for at least about 95% of particles.

In some embodiments, the pharmaceutical composition further comprises a seal coating between the capsule and the delayed release coating. The seal coating functions to seal and prepare the capsules for subsequent coating. The seal coating can be pH independent or pH dependent. A preferred example of a pH independent coating is HPMC. An example of a pH dependent seal coating is an aqueous dispersion of anionic polymers with methacrylic acid as a functional group, e.g., Eudragit L30-55. Both these seal coatings adhere well to the capsules and provide acceptable surfaces for further coating; however, Eudragit L30-55 protects the capsule longer in an acidic environment.

In some embodiments, the pharmaceutical composition further comprises an outer dye coating which provides the dosage unit with a color coating.

In some embodiments, the pharmaceutical compositions of the present invention have a dissolution profile such that about 80% to about 90% of the doxycycline salt is dissolved after about 30 minutes at pH of about 1.1. Also, the pharmaceutical compositions have a dissolution profile such that about 90% of the doxycycline salt is dissolved after about 120 minutes at pH of about 1.1 and 120 minutes at pH of about 6.0.

The present invention includes a method for treating the inflammatory lesions of rosacea in a human in need thereof. Inflammatory lesions of rosacea include papules and pustules of rosacea. The method comprises orally administering a once a day dose of a pharmaceutical composition of the present invention. That is, a unit dose form (i.e., a capsule) is administered daily.

The unit dose forms of the present invention are bioequivalent to a reference formulation. The reference formulation is a gelatin capsule filled with beads of doxycycline monohydrate, wherein the beads consist of 30 mg of immediate release beads and 10 mg of delayed release beads. For example, the reference formulation is a product for the treatment of the papules and pustules of rosacea sold by Galderma Laboratories, L.P. of Fort Worth, Tex. under the trademark Oracea®.

Bioequivalence herein is defined by the regulations of the United States Federal and Drug Administration. In particular, bioequivalence is found if the 90% Confidence Interval of the relative mean $C_{max}$, $AUC_{(0-t)}$ and $AUC_{(0-\infty)}$ of a pharmaceutical composition to the reference formulation is within 80.00% to 125.00% upon administration to humans in a fasting state and in a fed state, in a noncompartmental analysis with log transformed data.

An example of a fasting state is at least a ten hour fast prior to administration of a pharmaceutical composition.

The relative mean $C_{max}$ of a unit dosage form of the present invention is within 80.00% to 125.00% of the $C_{max}$ value of 510±220.7 ng/mL of Oracea®, after administration of a single dose to humans in a fasting state.

The relative mean $AUC_{(0-\infty)}$ of a unit dosage form of the present invention is within 80.00% to 125.00% of the $AUC_{(0-\infty)}$ value of 9227±3212.8 ng·hr/mL of Oracea®, after administration of a single dose to humans in a fasting state.

The relative mean $C_{max}$ of a unit dosage form of the present invention at steady state is within 80.00% to 125.00% of the $C_{max}$ value of 600±194.2 ng/mL of Oracea®, after administration to humans in a fasting state.

The relative mean $AUC_{(0-\infty)}$ of a unit dosage form of the present invention at steady state is within 80.00% to 125.00% of the $AUC_{(0-\infty)}$ value of 7543±2443.9 ng·hr/mL of Oracea®, after administration to humans in a fasting state.

Under fed conditions, $C_{max}$ and AUC Oracea® decrease about 30-50% and about 20-40%, respectively, or about 45% and about 25%, respectively. The $C_{max}$ and AUC of the unit dosage form of the present invention decrease commensurately under fed conditions.

In one embodiment, the $C_{max}$ of a unit dosage form of the present invention, after administration of a single dose to humans in a fasting state, has a range of about 200 ng/mL to about 1120 ng/mL. Examples of other preferred lower boundaries of this range include about 230, 250, 300, 350, 400, 450 and 500 ng/mL. Examples of other preferred upper boundaries of this range include about 500, 550, 600, 650, 700, 750, 800, 850, 900 and 950 ng/mL.

In one embodiment, the $AUC_{(0-\infty)}$ of a unit dosage form of the present invention, after administration of a single dose to humans in a fasting state, has a range of about 4800 ng·hr/mL to about 15,600 ng·hr/mL. Examples of other preferred lower boundaries of this range include about 5000, 5500, 6500, 7500, 8500, 9500 and 10,000 ng·hr/mL. Examples of other preferred upper boundaries of this range include about 10,000, 11,000, 12,000, 13,000, 14,000 and 15,000 ng·hr/mL.

In one embodiment, the $C_{max}$ of a unit dosage form of the present invention at steady state, after administration to humans in a fasting state, has a range of about 320 ng/mL to about 1000 ng/mL. Examples of other preferred lower boundaries of this range include about 350, 400, 450, 500, 550, 600 and 660 ng/mL. Examples of other preferred upper boundaries of this range include about 660, 750, 800, 850, 900 and 950 ng/mL.

In one embodiment, the $AUC_{(0-t)}$ of a unit dosage form of the present invention, at steady state, after administration to humans in a fasting state, has a range of about 3500 ng·hr/mL to about 12,500 ng·hr/mL. Examples of other preferred lower boundaries of this range include about 4000, 4500, 5500, 6500, 7500 and 8500 ng·hr/mL. Examples of other preferred upper boundaries of this range include about 8500, 9500, 10,500 and 11,500 ng·hr/mL.

Under fed conditions, $C_{max}$ and AUC of the unit dosage form of the present invention decrease about 30-50% and about 20-40%, respectively, or about 45% and about 25%, respectively.

The plasma concentrations of doxycycline achieved upon administration of unit dose forms of the present invention are less than the concentration required to treat bacterial diseases. Administration of the compositions for up to eighteen months demonstrates no detectable long term effects on bacterial flora of the oral cavity, skin, intestinal tract and/or vagina. For example, administration of a daily unit dose results in no reduction of skin microflora during a six-month treatment.

Preferably, upon a once-daily oral dosage of the pharmaceutical composition, a human is provided with blood levels of the doxycycline of about 0.3 µg/ml to about 0.8 µg/ml.

In one embodiment, the present invention also provides methods of treating acne. The method comprises orally administering a once a day dose of the pharmaceutical compositions of the present invention, i.e., a daily dose of a unit dose form. As used herein, the term "acne" is a disorder of the skin characterized by papules, pustules, cysts, nodules, comedones, and other blemishes or skin lesions. These blemishes and lesions are often accompanied by inflammation of the skin glands and pilosebaceous follicles, as well as, microbial, especially bacterial, infection.

For the purposes of this specification, acne includes all known types of acne. Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, and nodulocystic acne.

The pharmaceutical compositions of the present invention can be made as would be known by a skilled artisan. Examples of making the compositions can be found in U.S. patent application Ser. No. 12/466,261, incorporated herein by reference in its entirety.

EXAMPLES

Example 1

A Randomized, Single-Center, Single-Dose, Open-Label, Three-Way Crossover, Pivotal Bioequivalence Study of Doxycycline 36 mg Capsules and Doxycycline 38 mg Capsules Compared with ORACEA® (Doxycycline 40 mg) Capsules in Healthy Human Subjects Under Fasting Conditions The aim of the study was to compare the bioavailability of doxycycline "drug coated" capsules 36-mg and doxycycline "drug coated" capsules 38-mg of the present invention, relative to the reference product, the FDA approved 40-mg Oracea® capsule under fasting conditions. The study showed that the bioavailability of Doxycycline "drug coated" Capsules 36-mg and Doxycycline "drug coated" Capsules 38-mg, are bioequivalent to the reference product, the FDA approved 40-mg Oracea® capsule under fasting conditions.

Study Objectives

Pharmacokinetics objectives: Comparison of the rate and extent of absorption and exposure of two doses of doxycycline monohydrate capsules (Test products) with Oracea® 40-mg capsules (Reference product) in healthy subjects in order to determine bioequivalence under fasting conditions.

Safety objectives: tolerability and safety of single oral administrations of three dose levels of doxycycline capsules in healthy subjects under fasting conditions.

Study Design

The study was conducted according to an open-label, randomized, three-period crossover design with a wash-out phase of 7 days minimum. Subjects received a single dose of the test formulations (Treatment A, 36-mg capsule and treatment B, 38-mg capsule) and the reference (Treatment C, 40-mg capsule) products 30 minutes after an overnight fast (i.e. at least 10 hours) from food followed by a fast from food for at least 4 hours post-dose.

Summary of Study Results

Study Characteristics

The study was carried out in 44 healthy volunteers; however 5 subjects missed at least one treatment period, and these subjects were not considered for the bioequivalence assessment. Subject reasons for missing at least one treatment period include 2 cases of schedule conflicts, 2 for personal reasons and 1 Adverse Event of tonsillitis (unrelated to study drug). The study protocol was designed to ensure that a minimum of 38 subjects completed, and this was objective was achieved with 39 evaluable subjects.

Bioequivalence Assessment:

Blood samples for pharmacokinetic profiling were taken up to 96 hours post-dose, and doxycycline plasma concentrations were determined with a validated LC-MS/MS method, LOQ: 15 ng/mL.

The pharmacokinetic (PK) parameters for doxycycline were determined using a standard non-compartmental method, and $C_{max}$, $AUC_{0-t}$ (with t being the last quantifiable point), $AUC_{0-inf}$ were analyzed statistically using log-transformed data. Bioequivalence was assessed by examining the 90% confidence intervals for the ratio of the test formulation mean relative to the reference formulation mean.

Figure 2:
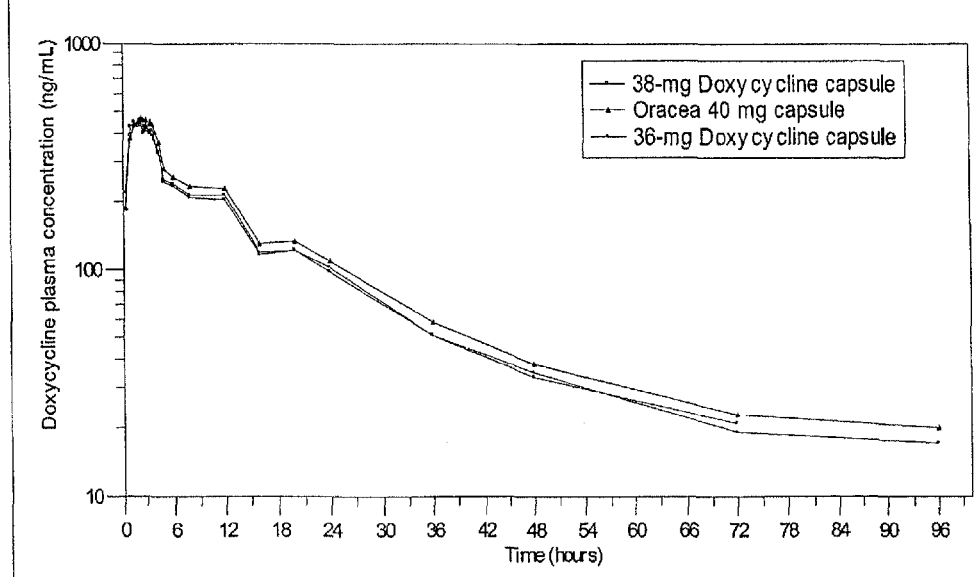
FIG. 2 is a graph showing the Mean (±SD) Plasma Doxycycline Concentration vs. Time Profiles in Log-linear Scale.

The mean and standard deviations for the PK parameters are provided in Tables 1 and 2 below, and the mean plasma profiles in normal scale and log scale are shown in FIGS. 1 and 2. The statistical analyses of PK results are summarized in Tables 3 and 4.

36-mg Doxycycline Capsule Vs. 40 mg Oracea Capsule:

The calculated 90% confidence intervals of the mean test/reference ratios of $C_{max}$, $AUC_{O-t}$, $AUC_{O-inf}$ were [92.73; 102.21], [87.03; 93.03] and [89.15; 97.75], respectively. Of note, the FDA guidance (*Bioavailability and Bioequivalence Studies for Orally Administered Drug Products—General Considerations*—March 2003) states that to be inside the acceptance interval, values should be at least 80.00 and no more than 125.00. Therefore, all tested PK parameters ($C_{max}$, $AUC_{0-t}$, $AUC_{0-inf}$) were strictly within the bioequivalence range of 80.00-125.00%.

38-mg Doxycycline Capsule Vs. 40 mg Oracea Capsule:

The calculated 90% confidence intervals of the mean test/reference ratios of $C_{max}$, $AUC_{0-t}$, $AUC_{0-inf}$ were [88.19; 98.47], [87.67; 94.28] and [86.80; 94.47], respectively. Therefore, all tested PK parameters ($C_{max}$, $AUC_{0-t}$, $AUC_{0-inf}$) were strictly within the bioequivalence range of 80.00-125.00%.

In conclusion, Doxycycline 36-mg capsule and 40-mg Oracea® capsule and Doxycycline 38-mg capsule and 40-mg Oracea® under fasting conditions are considered bioequivalent with respect to $C_{max}$, $AUC_{0-t}$ and $AUC_{0-inf}$ using the 80-125% FDA required criteria. Adverse events experienced were transient and mild to moderate in severity; they were also consistent with the known safety/tolerability profile of doxycycline.

TABLE 1

Overall pharmacokinetics parameters (Arithmetic mean ± SD)

| Parameters | N | 36-mg Doxycycline Capsule (TEST) | N | 40-mg Oracea ® Capsule (REFERENCE) |
|---|---|---|---|---|
| $AUC_{0-t}$ (ng.hr/mL) Mean ± SD Min-Max CV (%) | 39 | 6397 ± 1457 3936-10598 23% | 39 | 7101 ± 1451 3856-10418 20% |
| $AUC_{0-inf}$ (ng.hr/mL) Mean ± SD Min-Max CV (%) | 22 | 7151 ± 1184 4875-9673 17% | 31 | 7529 ± 1462 4437-11001 19% |
| $C_{max}$ (ng/mL) Mean ± SD Min-Max CV (%) | 39 | 504 ± 189 258-1113 38% | 39 | 514 ± 176 251-1056 34% |

AUC: area under the concentration time curve;
$C_{max}$: observed peak drug concentration;
Note:
$AUC_{0-inf}$ were calculated only for profiles meeting acceptance criteria in linear regression.

TABLE 2

Overall pharmacokinetics parameters (Arithmetic mean ± SD)

| Parameters | N | 38-mg Doxycycline Capsule (TEST) | N | 40-mg Oracea ® Capsule (REFERENCE) |
|---|---|---|---|---|
| $AUC_{0-t}$ (ng.hr/mL) | 39 | 6500 ± 1523 3488-10345 | 39 | 7101 ± 1451 3856-10418 |

TABLE 2-continued

Overall pharmacokinetics parameters (Arithmetic mean ± SD)

| Parameters | N | 38-mg Doxycycline Capsule (TEST) | N | 40-mg Oracea ® Capsule (REFERENCE) |
|---|---|---|---|---|
| Mean ± SD Min-Max CV (%) | | 23% | | 20% |
| $AUC_{0-inf}$ (ng.hr/mL) Mean ± SD Min-Max CV (%) | 29 | 7011 ± 1605 3962-10688 23% | 31 | 7529 ± 1462 4437-11001 19% |
| $C_{max}$ (ng/mL) Mean ± SD Min-Max CV (%) | 39 | 489 ± 199 212-1145 41% | 39 | 514 ± 176 251-1056 34% |

AUC: area under the concentration time curve;
$C_{max}$: observed peak drug concentration;
Note:
$AUC_{0-inf}$ were calculated only for profiles meeting acceptance criteria in linear regression.

TABLE 3

Summary of statistical analysis of pharmacokinetic data (36-mg v. 40-mg; N = 39)

| | Least Square Mean | | Geometric Mean[a] | | | 90% Confidence Interval | |
|---|---|---|---|---|---|---|---|
| | 36 mg Doxycycline Capsule | 40 mg Oracea ® Capsule | 36 mg Doxycycline Capsule | 40 mg Oracea ® Capsule | Ratio (%) | Lower Limit (%) | Upper Limit (%) |
| $AUC_{0-t}$ (ng * h/mL) | 8.744 | 8.849 | 6271.73 | 6970.06 | 89.98 | 87.03 | 93.03 |
| $AUC_{0-inf}$ (ng * h/mL) | 8.850 | 8.919 | 6972.21 | 7468.95 | 93.35 | 89.15 | 97.75 |
| $C_{max}$ (ng/mL) | 6.166 | 6.193 | 476.44 | 489.38 | 97.35 | 92.73 | 102.21 | a: Geometric means are based on least square means of ln-transformed values
N: Number of subjects included in PK analysis.

TABLE 4

Summary of statistical analysis of pharmacokinetic data (38-mg v. 40mg; N = 39)

| | Least Square Mean | | Geometric Mean[a] | | | 90% Confidence Interval | |
|---|---|---|---|---|---|---|---|
| | 38 mg Doxycycline Capsule | 40 mg Oracea ® Capsule | 38 mg Doxycycline Capsule | 40 mg Oracea ® Capsule | Ratio (%) | Lower Limit (%) | Upper Limit (%) |
| $AUC_{0-t}$ (ng * h/mL) | 8.754 | 8.849 | 6336.27 | 6969.69 | 90.91 | 87.67 | 94.28 |
| $AUC_{0-inf}$ (ng * h/mL) | 8.820 | 8.919 | 6769.67 | 7475.68 | 90.56 | 86.80 | 94.47 |
| $C_{max}$ (ng/mL) | 6.123 | 6.194 | 456.26 | 489.62 | 93.19 | 88.19 | 98.47 | a: Geometric means are based on least square means of ln-transformed values
N: Number of subjects included in PK analysis Example 2

A Randomized, Single-Center, Single-Dose, Open-Label, Three-Way Crossover, Pivotal Bioequivalence Study of Doxycycline 36 mg Capsules and Doxycycline 38 mg Capsules Compared with ORACEA® (Doxycycline 40 mg) Capsules in Healthy Human Subjects Under Fed Conditions The aim of the study was to compare the bioavailability of Doxycycline "drug coated" Capsules 36-mg and Doxycycline "drug coated" Capsules 38-mg, relative to the reference product, the FDA approved 40-mg Oracea® capsule under fed conditions. The bioequivalence study showed that the bioavailability of Doxycycline "drug coated" Capsules 36-mg and Doxycycline "drug coated" Capsules 38-mg, are bioequivalent to the reference product, the FDA approved 40-mg Oracea® capsule under fed conditions.

Study Objectives

Pharmacokinetics objectives: Comparison of the rate and extent of absorption and exposure of two doses of doxycycline monohydrate capsules (Test products) with Oracea® 40-mg capsules (Reference product) in healthy subjects in order to determine bioequivalence under fed conditions.

Safety objectives: tolerability and safety of single oral administrations of three dose levels of doxycycline capsules in healthy subjects under fed conditions.

Study Design

The study was conducted according to an open-label, randomized, three-period crossover design with a wash-out phase of 7 days minimum. Subjects received a single dose of the test formulations (Treatment A, 36-mg capsule and treatment B, 38-mg capsule) and the reference (Treatment C, 40-mg capsule) products 30 minutes after a 1000 calorie, high-fat and high-protein meal.

Summary of Study Results

Study Characteristics

The study was carried out in 44 healthy volunteers; one subject was excluded from the bioequivalence assessment due to a major deviation (subject vomited within a six-hour period following drug administration).

Bioequivalence Assessment:

Blood samples for pharmacokinetic profiling were taken up to 96 hours post-dose, and doxycycline plasma concentrations were determined with a validated LC-MS/MS method, LOQ: 15 ng/mL.

The pharmacokinetic (PK) parameters for doxycycline were determined using a standard non-compartmental method, and $C_{max}$, $AUC_{0-t}$ (with t being the last quantifiable point), $AUC_{0-inf}$ were analyzed statistically using log-transformed data. Bioequivalence was assessed by examining the 90% confidence intervals for the ratio of the test formulation mean relative to the reference formulation mean.

Figure 3:
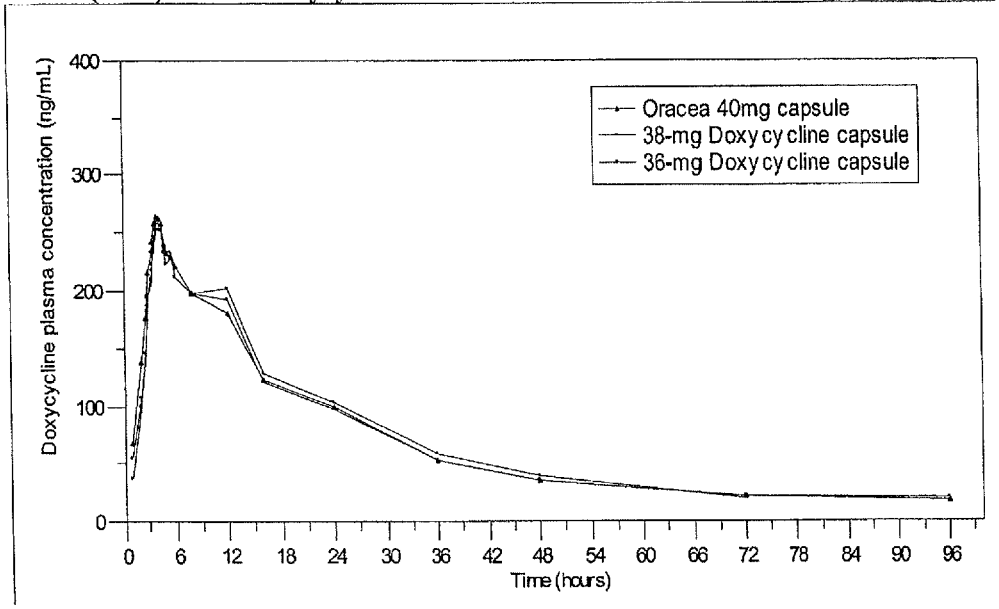
FIG. 3 is a graph showing the Mean (±SD) Plasma Doxycycline Concentration vs. Time Profiles using Normal scale.
Figure 4:
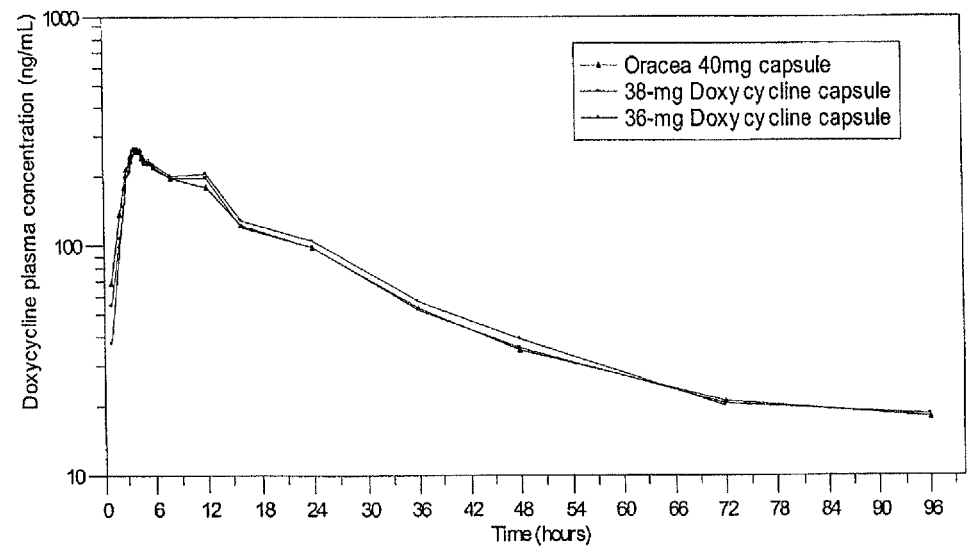
FIG. 4 is a graph showing the Mean (±SD) Plasma Doxycycline Concentration vs. Time Profiles in Log-linear Scale.
Figure 5:
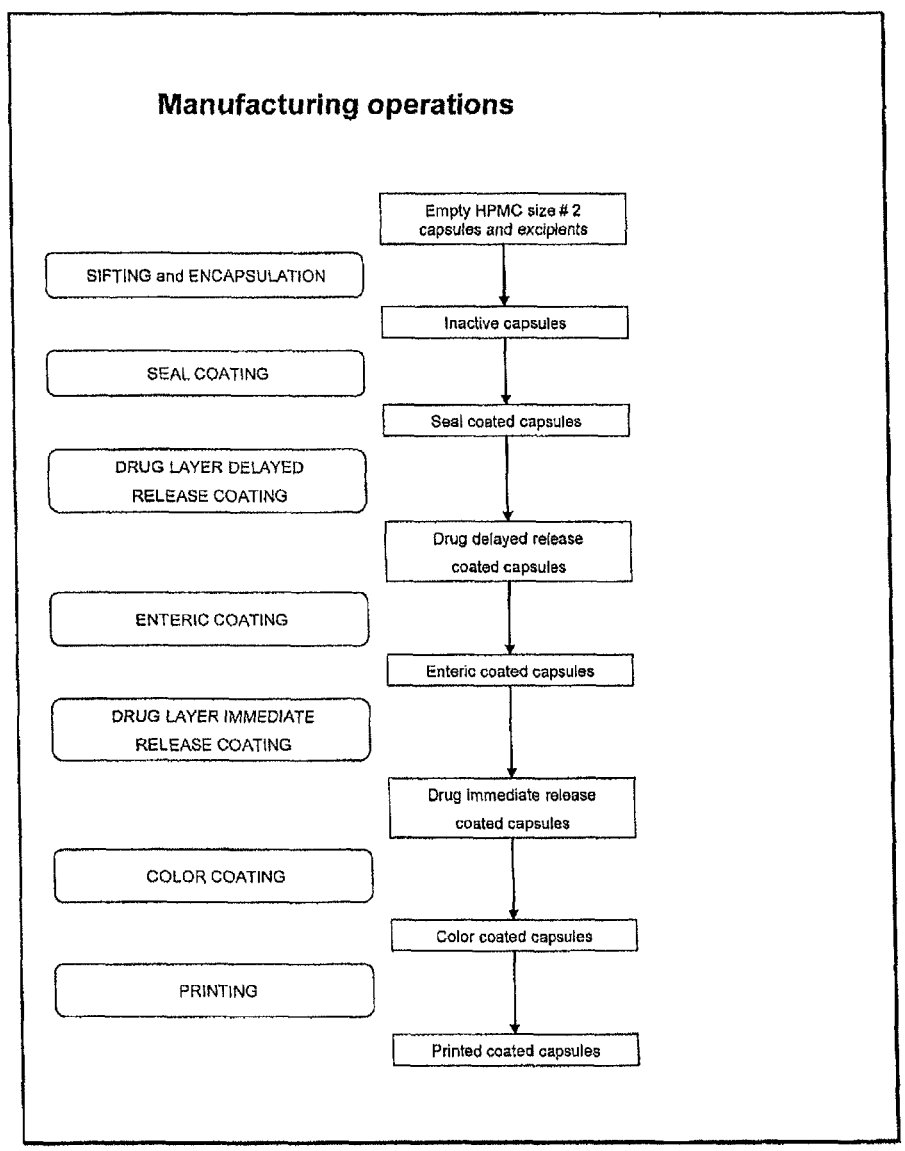
FIG. 5 is a flow chart outlining a manufacturing process for compositions of the present invention.

The mean and standard deviations for the PK parameters are provided in Tables 5 and 6 below, and the mean plasma profiles in normal scale and log scale are shown in FIGS. 3 and 4. The statistical analyses of PK results are summarized in Tables 7 and 8.

36-mg Doxycycline Capsule Vs. 40 mg Oracea Capsule:

The calculated 90% confidence intervals of the mean test/reference ratios (expressed in percentages) of $AUC_{0-t}$, $AUC_{O-inf}$, $C_{max}$ were [93.57; 100.18], [92.28; 100.34] and [96.51; 104.85], respectively. Of note, the FDA guidance (*Bioavailability and Bioequivalence Studies for Orally Administered Drug Products—General Considerations*—March 2003) stated that to be inside the acceptance interval, values should be at least 80.00 and no more than 125.00. Therefore, all tested PK parameters ($AUC_{0-t}$, $AUC_{O-inf}$, $C_{max}$) were strictly within the bioequivalence range of 80.00-125.00%.

38-mg Doxycycline Capsule Vs. 40 mg Oracea Capsule:

The calculated 90% confidence intervals of the mean test/reference ratios of, $AUC_{0-t}$, $AUC_{0-inf}$, $C_{max}$, were [97.50; 105.57], [100.92; 111.09] and [97.55; 108.99], respectively. Therefore, all tested PK parameters ($AUC_{0-t}$, $AUC_{O-inf}$, $C_{max}$) were strictly within the bioequivalence range of 80.00-125.00%.

In conclusion, Doxycycline 36-mg capsule and 40-mg Oracea capsule and Doxycycline 38-mg capsule and 40-mg Oracea® under fed conditions are considered bioequivalent with respect to $C_{max}$, $AUC_{O-t}$ and $AUC_{0-inf}$ using the 80-125% FDA required criteria.

Food effect: Concomitant administration of a 1000 calorie, high-fat, high-protein meal with doxycycline 36-mg capsule resulted in a decrease of the systemic exposure to doxycycline: the rate ($C_{max}$) and extent of absorption ($AUC_{0-t}$) are 42% and 17% lower than that observed in the study under fasting conditions (study # RD.06.SPR.18210). For the formulation containing 38-mg of doxycycline, the food effect was similar and the decrease in the $C_{max}$ and AUC0-t was by 38% and 13% respectively. However, the food effect on doxycycline pharmacokinetics is well known and the observed reductions in $C_{max}$ and $AUC_{0-t}$ in this study for Oracea (44% and 23%, respectively) were consistent with the drug approval package (NDA 50-805) for Oracea® (under fed conditions $C_{max}$ and $AUC_{0-t}$ decreased by 45% and 22%, respectively).

TABLE 5

Overall pharmacokinetics parameters (Arithmetic mean ± SD)

| Parameters | N | 36-mg Doxycycline Capsule (TEST) | N | 40-mg Oracea ® Capsule (REFERENCE) |
|---|---|---|---|---|
| $AUC_{0-t}$ (ng.hr/mL) Mean ± SD Min-Max CV (%) | 43 | 5312 ± 1626 2264-8922 31% | 43 | 5491 ± 1336 3673-8753 24% |
| $AUC_{0-inf}$ (ng.hr/mL) Mean ± SD Min-Max CV (%) | 28 | 5769 ± 1542 4022-10089 27% | 32 | 5793 ± 1146 4391-8794 20% |
| $C_{max}$ (ng/mL) Mean ± SD Min-Max CV (%) | 43 | 291 ± 94 155-524 32% | 43 | 288 ± 76 168-477 26% |

AUC: area under the concentration time curve;
$C_{max}$: observed peak drug concentration;
Note:
$AUC_{0-inf}$ were calculated only for profiles meeting acceptance criteria in linear regression.

TABLE 6

Overall pharmacokinetics parameters (Arithmetic mean ± SD)

| Parameters | N | 38-mg Doxycycline Capsule (TEST) | N | 40-mg Oracea ® Capsule (REFERENCE) |
|---|---|---|---|---|
| $AUC_{0-t}$ (ng.hr/mL) Mean ± SD Min-Max CV (%) | 43 | 5682 ± 1793 3680-10955 32% | 43 | 5491 ± 1336 3673-8753 24% |
| $AUC_{0-inf}$ (ng.hr/mL) Mean ± SD Min-Max CV (%) | 35 | 6241 ± 1681 4148-10846 27% | 32 | 5793 ± 1146 4391-8794 20% |
| $C_{max}$ (ng/mL) Mean ± SD Min-Max CV (%) | 43 | 304 ± 117 143-750 39% | 43 | 288 ± 76 168-477 26% |

AUC: area under the concentration time curve;
$C_{max}$: observed peak drug concentration;
Note:
$AUC_{0-inf}$ were calculated only for profiles meeting acceptance criteria in linear regression.

TABLE 7

Summary of statistical analysis of pharmacokinetic data (36-mg vs 40-mg)

| | Least Square Mean | | Geometric Mean[a] | | | 90% Confidence Interval | |
|---|---|---|---|---|---|---|---|
| | 36 mg Doxycycline Capsule | 40 mg Oracea ® Capsule | 36 mg Doxycycline Capsule | 40 mg Oracea ® Capsule | Ratio (%) | Lower Limit (%) | Upper Limit (%) |
| $AUC_{0-t}$ (ng.h/mL) | 8.545 | 8.577 | 5140.31 | 5309.42 | 96.81 | 93.57 | 100.18 |
| $AUC_{0-inf}$ (ng.h/mL) | 8.638 | 8.676 | 5640.28 | 5861.40 | 96.23 | 92.28 | 100.34 |
| $C_{max}$ (ng/mL) | 5.635 | 5.629 | 280.06 | 278.40 | 100.59 | 96.51 | 104.85 | a: Geometric means are based on least square means of ln-transformed values

TABLE 8

Summary of statistical analysis of pharmacokinetic data (38-mg vs 40-mg)

|  | Least Square Mean | | Geometric Mean[a] | | | 90% Confidence Interval | |
| --- | --- | --- | --- | --- | --- | --- | --- |
|  | 38 mg Doxycycline Capsule | 40 mg Oracea® Capsule | 38 mg Doxycycline Capsule | 40 mg Oracea® Capsule | Ratio (%) | Lower Limit (%) | Upper Limit (%) |
| $AUC_{0-t}$ (ng.h/mL) | 8.591 | 8.577 | 5385.53 | 5308.36 | 101.45 | 97.50 | 105.57 |
| $AUC_{0-inf}$ (ng.h/mL) | 8.704 | 8.646 | 6024.67 | 5689.95 | 105.88 | 100.92 | 111.09 |
| $C_{max}$ (ng/mL) | 5.658 | 5.627 | 286.45 | 277.81 | 103.11 | 97.55 | 108.99 | a: Geometric means are based on least square means of ln-transformed values

Safety

No Serious Adverse Events (SAEs) were reported.

There were no discontinuations due to AEs.

32 Adverse Events (AEs) were reported for this study, of which 13 were related to study drug.

These related AEs occurred in 10 subjects, and were mostly related to nervous system complaints (headache) and gastrointestinal system disturbances (nausea and vomiting). All related AEs were transient, and mild to moderate in severity; they were also consistent with the known safety/tolerability profile of doxycycline.

A summary of Treatment Emergent Adverse Events (TE-AEs) is provided in Table 9.

new safety or tolerability issues were raised that are not addressed in the approved labelling for Oracea® capsules.

Conclusion

The present bioequivalence study showed that the bioavailability of Doxycycline "drug coated" Capsules 36-mg and Doxycycline "drug coated" Capsules 38-mg, are bioequivalent to the reference product, the FDA approved 40-mg Oracea® capsule under fed conditions.

TABLE 9

Overall Summary of Treatment Emergent Adverse Events [Safety Population]

|  | 36 mg DQXVCycline Capsule (N = 44) | | | 30 mg Doxycycline Capsule (N = 44) | | | 40 mg Oracea ® Capule (N = 44) | | |
| --- | --- | --- | --- | --- | --- | --- | --- | --- | --- |
|  | n | (%) | E | n | (%) | E | n | (%) | E |
| An TEAEs | 8 | (18.2%) | 12 | 10 | (22.7%) | 15 | 3 | (6.8%) | 5 |
| Any Drug-Related TEAEs | 4 | (9.1%) | 5 | 5 | (11.4%) | 7 | 1 | (2.3%) | 1 |
| Any SAEs | 0 | (0.0%) | 0 | 0 | (0.0%) | 0 | 0 | (0.0%) | 0 |
| Any Drug-Related SAEs | 0 | (0.0%) | 0 | 0 | (0.0%) | 0 | 0 | (0.0%) | 0 |
| Any Deaths | 0 | (0.0%) | 0 | 0 | (0.0%) | 0 | 0 | (0.0%) | 0 |
| Any Drug-Related Deaths | 0 | (0.0%) | 0 | 0 | (0.0%) | 0 | 0 | (0.0%) | 0 |
| Any TEAEs Leading to Withdrawal | 0 | (9.0%) | 0 | 0 | (0.9%) | 0 | 0 | (0.0%) | 0 |
| Any SAEs Resulting in Early Termination | 0 | (0.0%) | 0 | 0 | (0.0%) | 0 | 0 | (0.0%) | 0 |

Note:

N: Number of Subjects in the Specified Group n: Number of Subjects reporting TEAEs %: Percentage based on N E: Number of TEAEs No pregnancies were reported.

Given the study design (single-dose, three-way crossover) and small sample size, it is self-evident that any safety findings are not fully representative of use in the recommended clinical setting in a larger population. Overall however, no Example 3

Batch Formula

The batch formula presented in the Table 10 shows an industrial batch size of 125 000 capsules of the present invention.

TABLE 10

Doxycycline coated capsules, 36 mg and 38 mg - Batch formula

| Ingredient | Doxycycline coated capsules, 36 mg Unit formula (350.8 mg) | Quantity per batch | Doxycycline coated capsules, 38 mg Unit formula (353.5 mg) | Quantity per batch |
|---|---|---|---|---|
| Inactive capsules | 263.5 mg | 32 938 g | 263.5 mg | 32 938 g |
| Seal coating (13.3 mg) | | | | |
| Methacrylic acid copolymer dispersion (Eudragit ® L3OD 55) | 11.1 mg | 4625 g | 11.1 mg | 4625 g |
| Triethyl citrate | 2.2 mg | 275 g | 2.2 mg | 275 g |
| Drug layer delayed release (5.39 mg for 36 mg capsules and 8.09 for 38 mg capsules) | | | | |
| Hydroxypropyl methylcellulose (Methocel E6LVCI) | 1.33 mg | 166 g | 2.00 mg | 249 g |
| Simethicone emulsion (Simethicone 30% emulsion) | 0.06 mg | 25 g | 0.09 mg | 38 g |
| Doxycycline (as monohydrate, micronized) | 4 mg | 500 g* | 6 mg | 750 g* |
| Enteric coating (18.5 mg) | | | | |
| Methacrylic acid copolymer dispersion (Eudragit ® L3OD 55) | 15.4 mg | 6417 g | 15.4 mg | 6417 g |
| Triethyl citrate | 3.1 mg | 391 g | 3.1 mg | 391 g |
| Drug layer immediate release (43.1 mg) | | | | |
| Hydroxypropyl methylcellulose (Methocel E6LVCI) | 10.6 mg | 1325 g | 10.6 mg | 1325 g |
| Simethicone emulsion (Simethicone 30% emulsion) | 0.49 mg | 204 g | 0.49 mg | 204 g |
| Doxycycline (as monohydrate, micronized) | 32 mg | 4000 g* | 32 mg | 4000 g* |
| Color coating (7 mg) | | | | |
| Opadry ® blue, Y-S-4258 | 7 mg | 875 g | 7 mg | 875 g |
| Printing | | | | |
| Opacode ® Monogramming Ink S-1-18089 White | QS | QS | QS | QS |

(\*) The required quantity of doxycycline monohydrate to be used (Q) is calculated taking into account the water content (M %) and the purity of the anhydrous drug substance (P %).

Example: for 500 g of doxycycline monohydrate required, the quantity to be used (Q) is as follows:

$$Q(g) = [500\ g * 100 * 100] / [P * (100 - M)]$$

For feasibility and demonstration batches, a 2% excess drug coating suspension (for delayed and immediate release layers) is prepared to compensate the processing loss and therefore, not added in the batch formula. From registration batches, the excess drug coating suspension will be of 3% based on feasibility and demonstration batches results.

Example 4

TABLE 11

Doxycycline coated capsules, 36 mg and 38 mg- Qualitative and quantitative compositions

| Ingredient | Doxycycline Capsules, 36 mg Unit formula (350.8 mg) | Doxycycline Capsules, 38 mg Unit formula (353.5 mg) |
|---|---|---|
| Inactive capsules | 1 (Approximately 263.5 mg) | 1 (Approximately 263.5 mg) |
| Seal coating (13.3 mg) | | |
| Methacrylic acid copolymer dispersion (Eudragit ® L300 55) | 11.1 mg | 11.1 mg |
| Triethyl citrate | 2.2 mg | 2.2 mg |
| Drug layer delayed release (5.39 mg for 36 mg capsules and 8.09 mg for 38 mg capsules) | | |
| Hydroxypropyl methylcellulose (Methocel E6LVC)s | 1.33 mg | 2.00 mg |

TABLE 11-continued

Doxycycline coated capsules, 36 mg and 38 mg- Qualitative and quantitative compositions

| Ingredient | Doxycycline Capsules, 36 mg Unit formula (350.8 mg) | Doxycycline Capsules, 38 mg Unit formula (353.5 mg) |
|---|---|---|
| Simethicone emulsion (Simethicone 30% emulsion) | 0.06 mg | 0.09 mg |
| Doxycycline | 4 mg | 6 mg |
| Enteric coating (18.5 mg) | | |
| Methacrylic acid copolymer dispersion (Eudragit ® L3OD 55) | 15.4 mg | 15.4 mg |
| Triethyl citrate | 3.1 mg | 3.1 mg |
| Drug layer immediate release (43.1 mg) | | |
| Hydroxypropyl methylcellulose (Methocel E6LVC)s) | 10.6 mg | 10.6 mg |
| Simethicone emulsion (Simethicone 30% emulsion) | 0.49 mg | 0.49 mg |
| Doxycycline | 32 mg | 32 mg |
| Color coating (7 mg) | | |
| Opadry ® blue, Y-S-4258 | 7 mg | 7 mg |
| Printing | | |
| Opacode ® Monogramming Ink S-1-18089 White | QS | QS |

Physicochemical and Biological Properties

The unit form doses of the present invention exhibit the same dissolution characteristics as Oracea® Capsules, 40 mg (30 mg immediate release and 10 mg delayed release) marketed by Galderma, and have a bioequivalent profile.

Dissolution Profiles

A pilot-scale batch (Batch PB714) of Doxycycline coated capsules, 40 mg (30 mg IR/10 mg DR) was manufactured, i.e., an outside coated capsule containing 40 mg doxycycline distributed in two layers: a pH dependent layer containing 10 mg doxycycline for delayed release and a layer containing 30 mg doxycycline for immediate release. This batch was used in PK study BE09/040-BE091041, to assess bioequivalence comparatively to Oracea capsules (Batch 0805129A).

The dissolution test used for the development is the one that is specified in the FDA/OGD website for Doxycycline capsules (delayed release) 40 mg, as described in Table 12.

The dissolution profiles of this formulation and Oracea capsules presented in FIG. 6 indicate that both formulations present a similar profile.

The dissolution profiles of two demonstration batches (Batch CD000911, capsules coated with 36 mg doxycycline drug substance: 4 mg in DR layer/32 mg in IR layer and Batch CD001111, capsules coated with 38 mg doxycycline drug substance: 6 mg in DR layer/32 mg in IR layer), tested according to the conditions described in Table 12 above are presented in FIG. 7 and FIG. 8.

Dissolution profiles performed as in-process controls on the capsules coated with only the delayed release layer (i.e. with 4 mg and 6 mg doxycycline for the 36 mg and 38 mg strengths, respectively) at the end of step 4 of the manufacturing process, before application of the immediate release drug coating layer are presented in FIG. 7.

TABLE 12

Dissolution conditions

| | | |
|---|---|---|
| Dissolution media | Buffer A, pH 1.1 | 40 mL concentrated HCl in 6000 mL of water |
| | Buffer B | 54.4 g potassium phosphate dibasic + 8.1 g NaOH pellets in 2000 mL of water |
| | Buffer C | 40 g NaOH pellets in 500 mL of water |
| Medium volume | 750 mL Buffer A (pH 1.1) | |
| | 950 mL Buffer B + Buffer C (pH 6.0) | |
| Medium temperature | 37° C. + 0.5° C. | |
| Apparatus | USP Apparatus ll (paddles) | |
| Paddle rotation | 75 RPM | |
| Dissolution time | 2 h at pH 1.1 (Buffer A) | |
| | 2 h at pH 6.0 (after addition of Buffer B + Buffer C) | |
| Sampling times | 30, 60, 120, 150, 180 and 240 minutes | |
| Assay method | UV 268 nm | |
| Cell path length | 0.5 cm | |
| Standard solution | 40 mg doxycycline HCl in 50 mL Buffer A, diluted to 1/25 in Buffer A | |
| | Final concentration: 0.032 mg/mL doxycycline HCl | |

Dissolution profiles performed on the finished drug product, i.e. the capsules coated with 36 mg and 38 mg doxycycline (4 mg DR/32 mg IR. and 6 mg DR/32 mg IR, respectively) are presented in FIG. 8.

The dissolution profiles indicate that approximately 80% to 90% of the total amount of doxycycline is released in 30 minutes at pH 1.1, i.e. the totality of the drug substance present in the immediate release layer.

After 240 minutes (120 minutes at pH 1.1 then 120 minutes at pH 6.0), approximately 90% of the total amount of doxycycline are dissolved, corresponding to the subsequent dissolution of the delayed release layers.

The dissolution profiles, the formulation and the manufacturing process of the capsules, confirm that this dosage form presents both immediate release and delayed release properties.

These formulations (capsules coated with 36 mg and 38 mg doxycycline (4 mg DR/32 mg IR, and 6 mg DR/32 mg IR, respectively)) are those intended to be tested in pivotal PK studies. They correspond to the industrial manufacturing process and batch size (125 000 capsules described above).

Pharmacokinetic Data

Doxycycline coated capsules, 40 mg (30 mg IR/10 mg/DR), were tested in a pharmacokinetic study under fasting and fed conditions, aimed to assess bioequivalence comparatively to Oracea® capsules.

The formulation was found bioequivalent to Oracea capsules, 40 mg (see FIG. 9); moreover, the results obtained suggested that bioequivalence could be fine-tuned with slightly different proportions of doxycycline.

A second study under fasting and fed conditions was then undertaken with two formulations respectively coated with 36 mg doxycycline (4 mg delayed release and 32 mg immediate release and) and 37.5 mg doxycycline (7.5 mg delayed release and 30 mg immediate release) comparatively to Oracea® Capsules, 40 mg. The formulation at 36 mg was found bioequivalent both under fasting and fed conditions while formulation at 37.5 mg was bioequivalent under fed conditions only (see FIG. 10 and FIG. 11).

Dissolution and PK Data Relationship

The dissolution profiles of the different formulations clearly display the presence of an immediate release layer and a delayed release layer in the doxycycline coated capsules.

The pharmacokinetic data display the part played by the ratio IR/DR in the formulation: the IR layer enhances $C_{max}$ and the DR layer enhances AUC (terminal slope).

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

We claim:

1. A pharmaceutical composition in unit dose form for orally delivering doxycycline to a human, the pharmaceutical composition comprising:
a capsule, wherein the capsule is coated with a delayed release layer; wherein the capsule does not contain an active ingredient; wherein the delayed release layer comprises about 4 to 6 mg of doxycycline, or a pharmaceutically acceptable salt thereof, and a binding agent, and wherein the delayed release layer is coated with an enteric coating;
wherein the enteric coating dissolves at pH of about 5 to 6, and wherein the enteric coating is coated with an immediate release layer; wherein the immediate release layer comprises about 32 mg of doxycycline, or a pharmaceutically acceptable salt thereof, and a binding agent, wherein the relative mean $C_{max}$ of the pharmaceutical composition is within 80.00% to 125.00% of a $C_{max}$ of 510±220.7 ng/mL, after administration of a single dose of the pharmaceutical composition to humans in a fasting state; and wherein the relative mean $AUC_{(0-\infty)}$ of the pharmaceutical composition is within 80.00% to 125.00% of a $AUC_{(0-\infty)}$ of 9227±3212.8 ng·hr/mL, after administration of a single dose of the pharmaceutical composition to humans in a fasting state.

2. The pharmaceutical composition of claim 1, wherein
the relative mean $C_{max}$ of the pharmaceutical composition at steady state is within 80.00% to 125.00% of a $C_{max}$ value of 600±194.2 ng/mL after administration to humans in a fasting state, and
wherein the relative mean $AUC_{(0-t)}$ of the pharmaceutical composition at steady state is within 80.00% to 125.00% of a $AUC_{(0-t)}$ value of 7543±2443.9 ng·hr/mL, after administration to humans in a fasting state.

3. The pharmaceutical composition of claim 1 wherein the delayed release layer comprises about 4 mg of doxycycline monohydrate.

4. The pharmaceutical composition of claim 1 wherein the delayed release layer comprises about 6 mg of doxycycline monohydrate.

5. The pharmaceutical composition of claim 1 wherein the doxycycline salt is micronized.

6. The pharmaceutical composition of claim 5 wherein the micronized doxycycline salt has less than about 10 μm distribution for at least about 90% of particles.

7. The pharmaceutical composition of claim 1 further comprising a seal coating between the capsule and the delayed release coating.

8. The pharmaceutical composition of claim 7 wherein the seal coating comprises a pH dependent ingredient, wherein the pH dependent ingredient dissolves at pH of about 5 to 6.

9. The pharmaceutical composition of claim 1 wherein the capsule contains about 200 mg to about 260 mg of at least one inert ingredient.

10. The pharmaceutical composition of claim 1 wherein the ratio of the binding agent to the doxycycline monohydrate in the delayed release layer is about 1:3.

11. The pharmaceutical composition of claim 1 wherein the ratio of the binding agent to the doxycycline monohydrate in the immediate release layer is about 1:3.

12. The pharmaceutical composition of claim 1 wherein the binding agent is hydroxypropyl methylcellulose (HPMC), hydroxyethyl cellulose (HEC), hydroxypropyl cellulose (HPC), carboxy methyl cellulose (CMC), or mixtures thereof.

13. The pharmaceutical composition of claim 1, having a dissolution profile such that about 80% to about 90% of the doxycycline monohydrate is dissolved after about 30 minutes at pH of about 1.1.

14. The pharmaceutical composition of claim 1, having a dissolution profile such that about 90% of the doxycycline monohydrate is dissolved after about 120 minutes at pH of about 1.1 and 120 minutes at pH of about 6.0.

15. The pharmaceutical composition of claim 1, further comprising an outer color coating.

16. The pharmaceutical composition of claim 1, wherein the capsule is hydroxypropyl methylcellulose.

17. The pharmaceutical composition of claim 1, wherein the 90% Confidence Interval of the relative mean $C_{max}$, $AUC_{(0-t)}$ and $AUC_{(0-\infty)}$ of the pharmaceutical composition to a reference formulation is within 80.00% to 125.00% upon administration to humans in a fasting state, wherein the reference formulation is a gelatin capsule filled with beads of doxycycline monohydrate, wherein the beads consist of 30 mg of immediate release beads and 10 mg of delayed release beads.

18. A method for treating papules and pustules of rosacea in a human in need thereof, comprising orally administering a once a day dose of a pharmaceutical composition to the human, the pharmaceutical composition comprising: a capsule, wherein the capsule is coated with a delayed release layer; wherein the capsule does not contain an active ingredient; wherein the delayed release layer comprises about 4 to 6 mg of doxycycline, or a pharmaceutically acceptable salt thereof, and a binding agent, and wherein the delayed release layer is coated with an enteric coating; wherein the enteric coating dissolves at pH of about 5 to 6, and wherein the enteric coating is coated with an immediate release layer; wherein the immediate release layer comprises about 32 mg of doxycycline, or a pharmaceutically acceptable salt thereof, and a binding agent, wherein the relative mean $C_{max}$ of the pharmaceutical composition is within 80.00% to 125.00% of a $C_{max}$ of 510±220.7 ng/mL, after administration of a single dose of the pharmaceutical composition to humans in a fasting state; and wherein the relative mean $AUC_{(0-\infty)}$ of the pharmaceutical composition is within 80.00% to 125.00% of a $AUC_{(0-\infty)}$ of 9227±3212.8 ng·hr/mL, after administration of a single dose of the pharmaceutical composition to humans in a fasting state.

19. The pharmaceutical composition of claim 18, wherein
the relative mean $C_{max}$ of the pharmaceutical composition at steady state is within 80.00% to 125.00% of a $C_{max}$ value of 600±194.2 ng/mL after administration to humans in a fasting state, and
wherein the relative mean $AUC_{(0-t)}$ of the pharmaceutical composition at steady state is within 80.00% to 125.00% of a $AUC_{(0-t)}$ value of 7543±2443.9 ng·hr/mL, after administration to humans in a fasting state.

20. The method of claim 18, wherein the pharmaceutical composition further comprises a seal coating between the capsule and the delayed release coating.

21. The method of claim 20, wherein the seal coating comprises a pH dependent ingredient, wherein the pH dependent ingredient dissolves at pH of about 5 to 6.

22. The method of claim 18, wherein the capsule contains about 200 mg to about 260 mg of inert excipients.

23. The method of claim 18 wherein the delayed release layer comprises about 4 mg of doxycycline monohydrate.

24. The method of claim 18 wherein the delayed release layer comprises about 6 mg of doxycycline monohydrate.

25. The method of claim 18 wherein the doxycycline monohydrate is micronized, and wherein the micronized doxycycline monohydrate has less than about 10 μm distribution for at least about 90% of particles.

26. The method of claim 17, wherein the pharmaceutical composition has a dissolution profile such that about 80% to about 90% of the doxycycline salt is dissolved after about 30 minutes at pH of about 1.1.

27. The method of claim 18, wherein the pharmaceutical composition has a dissolution profile such that about 90% of the doxycycline salt is dissolved after about 120 minutes at pH of about 1.1 and 120 minutes at pH of about 6.0.

28. A pharmaceutical composition in unit dose form for orally delivering doxycycline to a human, the pharmaceutical composition comprising: a capsule, wherein the capsule is coated with a delayed release layer; wherein the capsule does not contain an active ingredient; wherein the delayed release layer comprises about 4 to 6 mg of doxycycline, or a pharmaceutically acceptable salt thereof, and a binding agent, and wherein the delayed release layer is coated with an enteric coating; wherein the enteric coating dissolves at pH of about 5 to 6, and wherein the enteric coating is coated with an immediate release layer; wherein the immediate release layer comprises about 32 mg of doxycycline, or a pharmaceutically acceptable salt thereof; and wherein after administration of a single dose to humans in a fasting state, the $C_{max}$ has a range of about 230 ng/mL to about 1120 ng/mL, and the $AUC_{(0-\infty)}$ has a range of about 4800 ng·hr/mL to about 15,600 ng·hr/mL.

29. The pharmaceutical composition of claim 28 wherein at steady state the $C_{max}$ has a range of about 325 ng/mL to about 1000 ng/mL, and the $AUC_{(0-t)}$ has a range of about 3500 ng·hr/mL to about 12,500 ng·hr/mL.

* * * * *

UNITED STATES PATENT AND TRADEMARK OFFICE
CERTIFICATE OF CORRECTION

PATENT NO. : 8,652,516 B1  
APPLICATION NO. : 13/929598  
DATED : February 18, 2014  
INVENTOR(S) : Etchegaray et al.

Page 1 of 1

It is certified that error appears in the above-identified patent and that said Letters Patent is hereby corrected as shown below:

IN THE SPECIFICATION:

Column 5, line 57:
  Now reads: "AUC(0-∞)"
  Should read: -- AUC(0-t) --

Column 5, line 59:
  Now reads: "AUC(0-∞)"
  Should read: -- AUC(0-t) --

Signed and Sealed this
Twelfth Day of August, 2014

Michelle K. Lee
*Deputy Director of the United States Patent and Trademark Office*